US00PP27299P3

(12) United States Plant Patent
Ballington et al.

(10) Patent No.: US PP27,299 P3
(45) Date of Patent: Oct. 25, 2016

(54) BLACKBERRY NAMED 'VON'

(50) Latin Name: ***Rubus* L. subgenus *Rubus* Watson.**
Varietal Denomination: Von

(71) Applicant: North Carolina State University, Raleigh, NC (US)

(72) Inventors: James Ralph Ballington, Cary, NC (US); Gina Elizabeth Fernandez, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 119 days.

(21) Appl. No.: 14/121,381

(22) Filed: Aug. 27, 2014

(65) Prior Publication Data

US 2016/0066489 P1 Mar. 3, 2016

(51) Int. Cl.
*A01H 5/08* (2006.01)

(52) U.S. Cl.
USPC ..... Plt./203

(58) Field of Classification Search
USPC ..... Plt./203
See application file for complete search history.

(56) References Cited

PUBLICATIONS

Fernandez et al 'Von' Thornless Blacberry. HortScience May 13 vol. 48 No. 5 654-656.*
Fernandez 'Von' Blackberry Cultivar NC Cooperative Extension. Oct. 23, 2012.*
U Fernandez et al 'Von' Thornless Blaeberry. HortScience May 13, 2013 vol. 48 No. 5 654-1.*
European CPVO Application No. A201600397, for variety "NC430", 10 pages, filed on Apr. 15, 2016.

* cited by examiner

*Primary Examiner* — Annette Para
(74) *Attorney, Agent, or Firm* — Myers Bigel & Sibley, P.A.

(57) ABSTRACT

'Von' is a new and distinct blackberry (*Rubus* L. subgenus *Rubus* Watson) cultivar, which originated as an open-pollinated seedling from bulked seed collected from a population of $F_1$ seedlings from the cross of NC 194 (non-patented)× Navaho (U.S. Plant Pat. No. 6,679, expired). This new blackberry cultivar can be distinguished by its high yields, large uniform fruit size, great fruit quality, mid- to late season fruit ripening, prolific fruiting row establishment, excellent shelf life and healthy plants.

4 Drawing Sheets

Latin name of the genus and species: The Latin name of the novel blackberry cultivar disclosed herein is *Rubus* L. subgenus *Rubus* Watson.

Variety denomination: The inventive cultivar of *Rubus* L. subgenus *Rubus* Watson disclosed herein has been given the varietal denomination 'Von'.

BACKGROUND OF THE INVENTION

A new cultivar of blackberry called 'Von' is described herein. The new cultivar originated as an open-pollinated seedling from bulked seed collected from a population of $F_1$ seedlings from the cross of NC 194 (non-patented)×Navaho (U.S. Plant Pat. No. 6,679, expired) located at the Upper Piedmont Research Station, Reidsville, N.C. in 1995. The seeds resulting from this uncontrolled hybridization were germinated in a greenhouse in the spring of 1996 and planted in a field at the Sandhills Research Station, Jackson Springs, N.C. The seedlings fruited during the summer of 1998, and one seedling, designated NC 430, was selected for its late season of ripening, large uniform fruit size, excellent fruit quality, excellent plant health, and thornless canes.

In the summer of 1998, the original plant selection was first propagated asexually from leafy stem cuttings, in Raleigh, N.C., and initially a test plot of 10 plants was established at the Upper Piedmont Research Station, Reidsville, N.C. in 1999. Subsequently, a replicated trial planting was established with asexually propagated plants at the Piedmont Research Station, Salisbury, N.C. in 2007. In 2009, two additional replicated trials were established at the Upper Mountain Research Station, Laurel Springs, N.C. and at the Mountain Horticultural Crops Research Station, Mills River, N.C. Additionally, the cultivar has been tested at farmer test plots in Rocky Point N.C., Hendersonville, N.C., Bailey, N.C. and at State or Federal Research Stations in OR and AR. At each location, propagation was from leafy stem cuttings from the Salisbury N.C. test plot.

The new cultivar has been asexually multiplied annually since 1999 by the use of leafy stem cuttings and by adventitious shoots from root cuttings. During all asexual multiplication, the characteristics of the original plant have been maintained and no aberrant phenotypes have appeared. Thus, test plantings over a wide geographic area have shown this new cultivar to be adapted to differing soil and climatic conditions. The new cultivar has been named the 'Von' cultivar.

SUMMARY OF THE INVENTION

'Von' is a new and distinct blackberry (*Rubus* L. subgenus *Rubus* Watson) cultivar, which can be distinguished by its high yields, large uniform fruit size, great fruit quality, late season fruit ripening, prolific fruiting row establishment, excellent shelf life and healthy plants.

BRIEF DESCRIPTION OF THE DRAWINGS

This new blackberry cultivar is illustrated by the accompanying photographs, which show the plant's form, foliage and fruit. These photographs show typical specimens of the new variety in color as nearly true as it is reasonably possible to make in a color illustration of this character. Colors in the photographs may differ slightly from the color values cited in the detailed botanical description, which accurately describe the colors of the new *Rubus* L. subgenus *Rubus* Watson cultivar. All photographs were taken of three year-old plants growing at the Piedmont Research Station, Salisbury, N.C. in 2010.

DETAILED BOTANICAL DESCRIPTION

Figure 1:
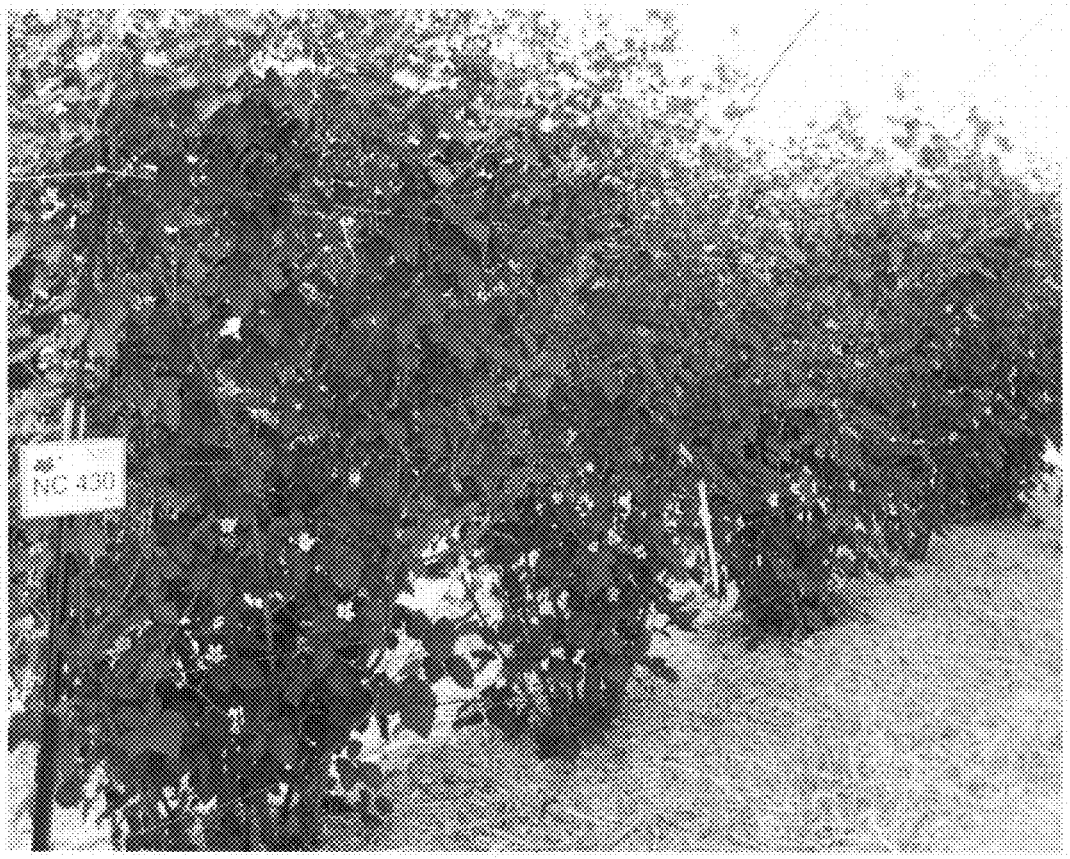
FIG. 1 is a color photograph showing a blackberry plant of the cultivar 'Von'.

The following is a detailed description of the botanical and pomological characteristics of the new and distinct cultivar of *Rubus* L. subgenus *Rubus* Watson plant known by the denomination 'Von'. Color notations are based on The Royal Horticultural Society Colour chart, The Royal Horticultural Society, London, UK, 5th edition, 2007. Where dimensions, sizes, colors and other characteristics are given, it is to be understood that such characteristics are approximations of averages set forth as accurately as practicable.

Plants used for botanical data were 4 years old and grown at the Piedmont Research Station near Salisbury, N.C. in a Cecil sandy clay soil. Water was supplied with drip tape irrigation. The plants were fertilized annually with nitrogen fertilizer and grown in a V-trellis training system. Weeds were controlled with pre- and post-emergence herbicides. A single application of liquid lime sulfur was applied to the plants in late winter.

Technical Description of the Variety

Plant:

*Size*.—Large; the average size of the plant is 4-6 ft tall and 3-4 wide in the spring before fruiting.

*Growth habit*.—Vigorous, with moderate suckering from crowns, moderate suckering from roots, canes erect to semi-erect.

*Productivity*.—High and for duration of six weeks; consistent from year to year. Yields averaged 26.5 lb/plant, which was statistically comparable to 'Navaho' (U.S. Plant Pat. No. 6,679, expired) (Table 1).

*Cold hardiness*.—Hardy to −12° C. (10° F.) comparable to 'Navaho'.

*Canes*.—Thornless, erect to semi-erect. Floricane (dormant or winter cane) diameter: base 2.83 cm, midpoint 2.56 cm, terminal 1.32 cm. Primocane (current season cane, late season) diameter: base 2.24 cm, midpoint 1.74 cm, terminal 1.23 cm. Floricane Internode length: base 13.69 cm, midpoint 7.65 cm, terminal 5.23 cm. Primocane Internode length: base 13.12 cm, midpoint 5.32 cm, terminal 6.54 cm. Floricane color: base N 199 A; midpoint — 199 A; terminus — 199 A. Primocane color: base — 144 A; midpoint — 144 A; terminus — 144 A. Date of primocane emergence: May 3.

Foliage:

*Floricane*.—Leaves: Mature compound leaf: Width 90.34 cm; length 106.86 cm. Leaflet: Width 40.33 cm; length 55.33 cm; shape cordate with acuminate apex and cordate base; margin serrated, serration teeth length 0.61 cm, and width at base 0.72 cm; very light pubescence on abaxial surface. Number of leaflets per compound leaf: 3. Color: Base abaxial: 147 B; adaxial: 147 A; midpoint abaxial: 147 B; adaxial: 147 A; terminal abaxial: 147 B; adaxial: 147 A. Petioles: Length: 36.6 cm. Color: 146 B. Petiolules: Length: 5.16 cm. Color: 146 B.

Figure 2:
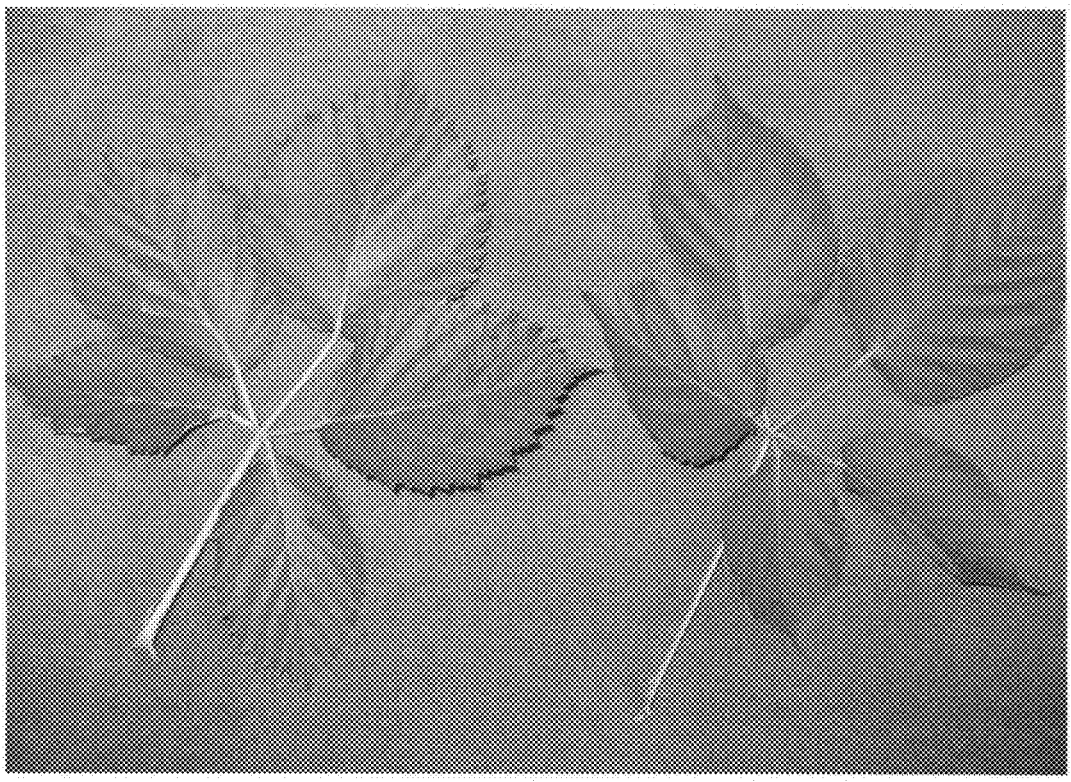
FIG. 2 is a color photograph showing the upperside of a primocane leaf of the cultivar 'Von'.

*Primocane*.—Leaves: (see FIG. 2). Mature compound leaf: Width 219.24 cm; length 232.25 cm. Leaflet: width 67.75 cm; length 88.97 cm; shape cordate, with acuminate apex and cordate base; margin serrated, with serration teeth length 0.56 cm and width at base 0.67 cm; light pubescence on abaxial surface. Number of leaflets per compound leaf: 5. Color: base abaxial: 147 B; adaxial: 147 A; midpoint abaxial: 147 B; adaxial: 147 A; terminal abaxial: 147 B; adaxial: 147 A. Petioles: Length: 112.1 cm. Color: 146 B. Petiolules: Length 28.7 cm. Color: 146 B.

Flowers:

*Date of bloom*.—First — Julian 108 (April 17); 50% — Julian 115 (April 24); Last — Julian 129 (May 8).

*Blossom color*.—N 155 D.

*Reproductive organs*.—Stamens: erect, numerous. Pistils: numerous. Pollen: normal and abundant. Self-fertile.

*Flower diameter*.—0.8 cm.

*Petal size*.—Length: 1.6 cm. Width: 1 cm.

*Number flowers per cluster*.—Mean of 14 with range of 7 to 18.

*Number of petals per flower*.—5.

*Number of sepals per flower*.—5.

*Peduncle length*.—0.81 cm.

*Peduncle color*.—146B.

*Cyme type*.—Elongate simple cyme.

Figure 3:
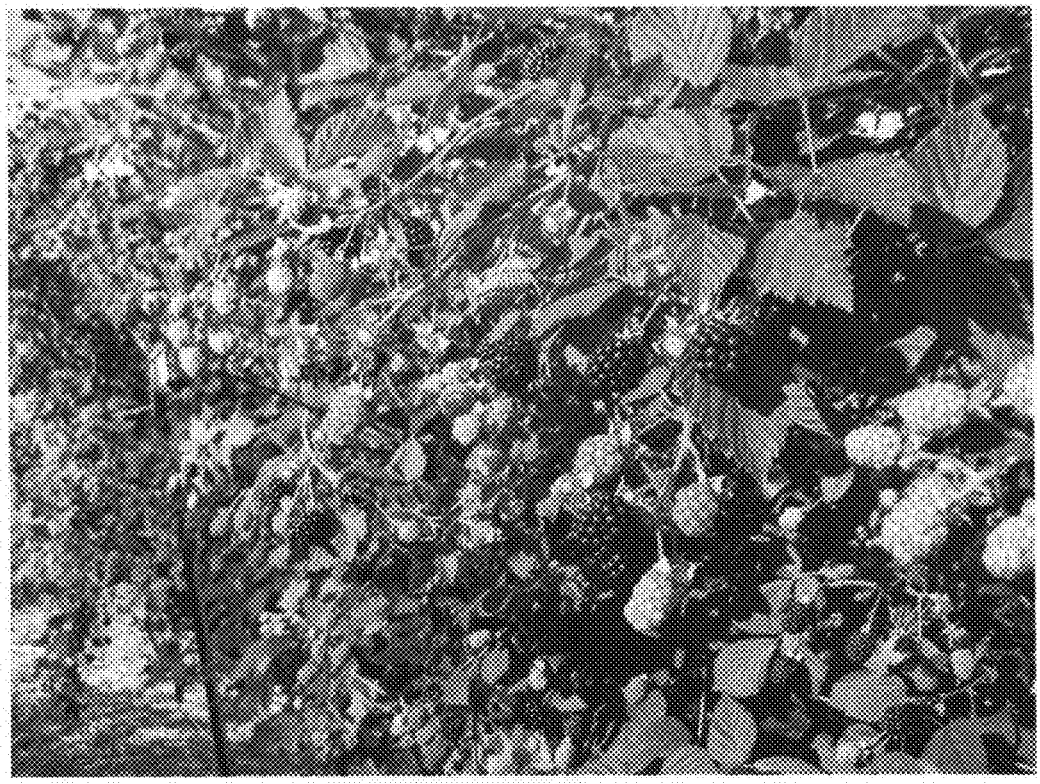
FIG. 3 is a color photograph showing blackberry fruit on the cultivar 'Von'.
Figure 4:
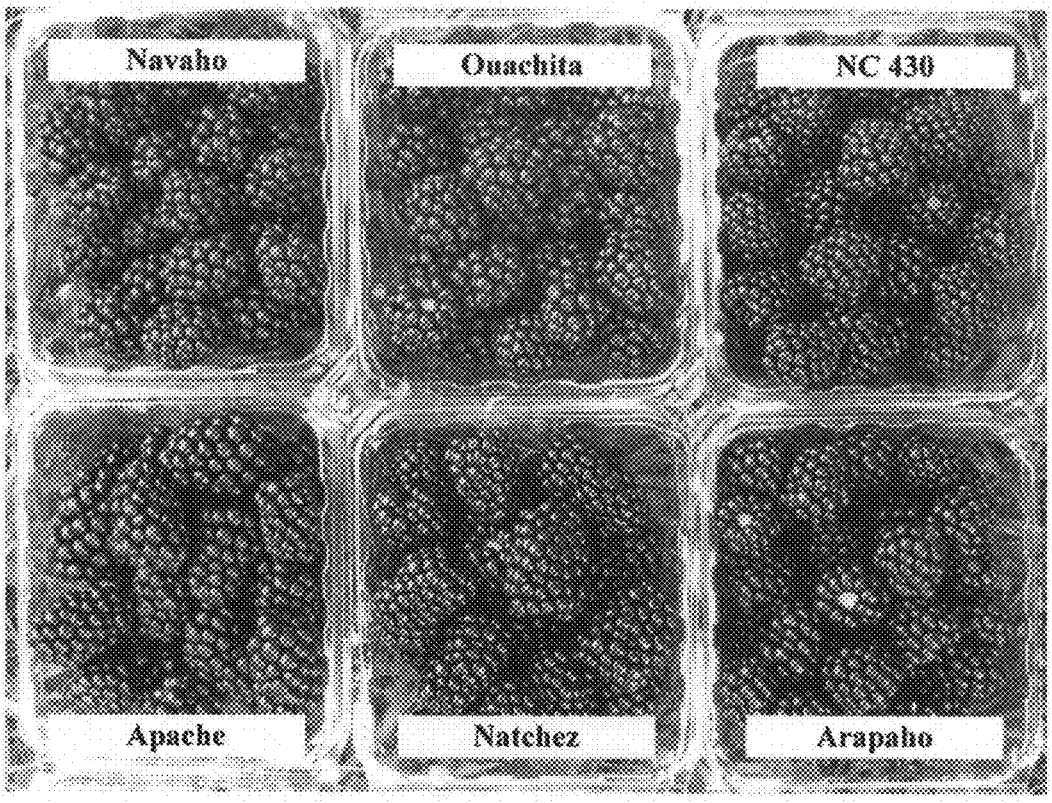
FIG. 4 is a color photograph showing three blackberries from the cultivar 'Von'.

Fruit: (see, FIG. 3 and FIG. 4).

*Maturity*.—Mid to late season. Average first ripe date is about June 22. Average period of ripening is about June 22 to August 2.

*Size*.—Medium, average 6.6 g, uniform. Diameter: Fruit at primary position on inflorescence: equator 2.32 cm, base pole 2.4 cm, terminal pole 1.99 cm; fruit at secondary positions on inflorescence: equator 2.29 cm., base pole 2.33 cm, terminal pole 1.87 cm. Length (Primary fruit) 2.48 cm.

*Shape*.—Medium, cylindrical, uniform.

*Color*.—Glossy black; 203A.

*Drupelet size*.—Small, 0.38 cm.

*Seed size*.—Length 3.6 mm, width 1.0 mm, Height 1.89 mm 2.86 mg (dry wt., individual seed) (Table 3).

*Soluble solids*.—9.4%. pH: 3.57 (as measured by pH meter on undiluted juice from a sample of 25 fully-ripe berries).

*Processed quality*.—Not evaluated in processing.

*Uses*.—Fresh is main use but can be processed for jellies, jams, juice, wine.

Disease reaction: No anthracnose, orange rust or double blossom/rosette observed on 'Von' plants in trial plots where these diseases were observed on other cultivars.

Comparison With Parental Plants

Plants and fruit of this new cultivar differ phenotypically from its parents. The new cultivar is late ripening, has high fruit quality and small drupelet and seed size, and high yields. 'Von' retains uniform fruit size throughout the harvest season. Although blackberries (*Rubus* subgenus *Rubus*) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry) possibly introgressed with *R. argutus* Link. (tall blackberry). The genes for thornlessness in the new cultivar, 'Von,' were derived from the British cultivar 'Merton Thornless' (non-patented), a derivative of *Rubus ulmifolius* Schott.

Plants of the new cultivar 'Von' are vigorous and prolific and row establishment following planting is rapid (FIG. 1). Both primocanes and floricanes are erect in growth habit. The canes can benefit from the use of a trellis with supporting wires to prevent canes from falling over due to wind or heavy fruit-loads. The plants are genetically thornless, having the recessive genes for thornless derived from the cultivar 'Navaho'. Plants have not exhibited symptoms of anthracnose [*Elsinoe veneta* (Burkh.) Jenkins], orange rust [*Gymnoconia nitens* (Schwein.) F. Kern and H. W. Thurston.] or double blossom/rosette [*Cercosporella rubi* (Wint.) Plakidas]. The bloom period of the new cultivar averages 2 to 3 days later than the cultivar Navaho.

Fruit yields averaged over three years are usually about 12,017 g/plant (26 lb/plant) and are comparable or higher than commercially available cultivars at test locations (Table 1). Yields are lower than others in the first year, but are as high or higher than other cultivars in subsequent years (Table 1). Fruit of the 'Von' cultivar begins ripening 3 days earlier than the fruit of the cultivar 'Navaho', and both have a similar fruiting period with average 44 days. Average first ripening date is June 22 at the Piedmont Research Station, Salisbury, N.C. (Table 2).

The fruit are glossy and cylindrical in shape, glossy black in color and very attractive. The fruit are large (6.6 g) and 1.5 to 1.7 g larger than the size of the fruit of the 'Navaho' cultivar. Fruit size of the new cultivar, 'Von', is maintained well throughout the entire harvest season. The new cultivar exhibits excellent fruit fertility with full drupelet. Drupelet and seeds are smaller than most other commercial cultivars (Table 3). The fruit is very firm at maturity, rating near that of 'Navaho' (non-patented), and 'Ouachita' (U.S. Plant Pat. No. 17,162). Storage ability of fresh fruit of the new cultivar is better to that of 'Navaho', 'Apache' (U.S. Plant Pat. No. 11,865), and 'Ouachita' cultivars.

The fresh fruit rates good in flavor. The flavor is sweet and mildly acidic, with a distinct blackberry aroma. The soluble solids concentration averages 9.4 to 10.4% on shiny black fruit, being comparable 'Apache', 'Arapaho', 'Ouachita' and 'Natchez'. The pH of 'Von' fruit juice is 3.57, which is lower than that of most commercial cultivars.

The high soluble solid concentration and high pH (i.e., low acid), characterize 'Von' as sweet with low acid. Dry seed weight averages 2.8 mg/seed, and seeds are smaller to those of 'Natchez', 'Navaho' and 'Ouachita' (Table 3).

Fruit clusters are medium, cymose, and are mostly borne on the periphery of the plant canopy, providing easy access to harvest. Flower fertility is high and clusters are well filled.

Distinctive features of the cultivar 'Von' are its high yields, mid to late season fruit ripening, and small seed size.

TABLE 1

Total yield of six blackberry cultivars grown in Salisbury, NC from 2008-2010 (lb/plant).

| Cultivar | 2008<br>2008 | 2009<br>2009 | 2010<br>2010 | Mean<br>Mean |
|---|---|---|---|---|
| 'Apache' | 12.0 b | 20.5 b | 12.5 cd | 15.0 b |
| 'Arapaho' | 7.8 c | 9.3 c | 8.6 d | 8.5 c |
| 'Natchez' | 8.2 c | 13.2 bc | 16.6 bc | 12.7 bc |
| 'Navaho' | 21.8 a | 28.2 a | 22.3 bc | 24.1 a |
| 'Von' | 10.9 bc | 29.7 a | 38.8 a | 26.5 a |
| 'Ouachita' | 12.6 b | 13.8 bc | 8.8 d | 11.7 bc |

Mean separation Tukey's HSD $p < 0.05$.

TABLE 2

Average harvest date at 5, 50 and 95 percent total yield 2008-2010 combined (%).

| Genotype | Tunnel | Tunnel | Tunnel |
|---|---|---|---|
| 'Apache' | 26-Jun b | 16-Jul b | 5-Aug b |
| 'Arapaho' | 31-May a | 13-Jun a | 1-Jul a |
| 'Natchez' | n/a | n/a | n/a |
| 'Navaho' | 23-Jun b | 19-Jul b | 12-Aug b |
| 'Von' | 22-Jun b | 13-Jul b | 5-Aug b |
| 'Ouachita' | 17-Jun b | 7-Jul b | 27-Jul b |

Mean separation Tukey's HSD $p < 0.05$.

TABLE 3

Seed number, weight and dimensions of five floricane fruiting blackberries.

| | Average no. seeds/fruit | Seed wt. (mg/100 seeds) | Seed height (mm) | Seed width (mm) | Seed length (mm) |
|---|---|---|---|---|---|
| 'Chester | 35 | 294 c | 2.3 a | 1.2 b | 3.4 ab |
| 'Natchez' | 101 | 352 ab | 2.5 a | 1.2 a | 3.8 ab |
| 'Navaho' | 56 | 590 b | 2.4 a | 1.3 ab | 3.5 a |
| 'Ouachita' | 53 | 374 a | 2.2 a | 1.1 b | 3.4 bc |
| 'Von' | 61 | 286 c | 1.9 b | 1.0 ab | 3.6 c |

Mean separation Tukey's HSD $p < 0.05$

What is claimed is:

1. A new and distinct cultivar of blackberry plant named 'Von', substantially as illustrated and described herein.

* * * * *